(12) United States Patent
Friedman et al.

(10) Patent No.: US 7,258,687 B2
(45) Date of Patent: Aug. 21, 2007

(54) DEVICE AND METHOD FOR INDUCING VASCULAR INJURY AND/OR BLOCKAGE IN AN ANIMAL MODEL

(75) Inventors: Beth Friedman, La Jolla, CA (US); David Kleinfeld, La Jolla, CA (US); Patrick D. Lyden, San Diego, CA (US); Nozomi Nishimura, La Jolla, CA (US); Christopher B. Schaffer, La Jolla, CA (US); Lee Frederick Schroeder, San Diego, CA (US); Philbert Tsai, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 124 days.

(21) Appl. No.: 10/538,548

(22) PCT Filed: Dec. 11, 2003

(86) PCT No.: PCT/US03/39428

§ 371 (c)(1),
(2), (4) Date: Jun. 10, 2005

(87) PCT Pub. No.: WO2004/052181

PCT Pub. Date: Jun. 24, 2004

(65) Prior Publication Data

US 2006/0142746 A1    Jun. 29, 2006

Related U.S. Application Data

(60) Provisional application No. 60/432,371, filed on Dec. 11, 2002.

(51) Int. Cl.
*A61B 18/20* (2006.01)
*A61B 5/02* (2006.01)

(52) U.S. Cl. .................. 606/11; 128/898; 600/504; 606/1

(58) Field of Classification Search ............. 128/898; 606/1–19; 600/400–550; 250/459.1; 372/22
See application file for complete search history.

(56) References Cited

U.S. PATENT DOCUMENTS 5,034,613 A * 7/1991 Denk et al. ............ 250/458.1

(Continued)

FOREIGN PATENT DOCUMENTS

WO    WO 03/060477 A2    7/2003

OTHER PUBLICATIONS

Mitra, P., et al., "Analysis of Dynamic Optical Imaging Data", *Imaging Neurons: A Laboratory Manual* (R. Yuste, et al., editors), 1999, pp. 9.1-9.9, Cold Spring Harbor Laboratory Press.

(Continued)

*Primary Examiner*—Henry M Johnson, III
(74) *Attorney, Agent, or Firm*—Eleanor M. Musick; Procopio, Cory, Hargreaves & Savitch LLP

(57) ABSTRACT

Ultrashort laser pulses are used to induce photodisruptive breakdown in vasculature in an animal to controllably produce hemorrhage, thrombosis or breach of the blood-brain barrier in individual, specifically-targeted blood vessels. Damage is limited to the targeted vessels such that neighboring vessels exhibit no signs of vascular damage, including vessels directly above and directly below the targeted vessel. Ultrashort laser pulses of lower energy are also used to observe and quantify the baseline and altered states of blood flow. Observation and measurement may be performed by TPLSM, OCT or other known techniques, providing a real-time, in vivo model for the dynamics and effects of vascular injury.

46 Claims, 4 Drawing Sheets

U.S. PATENT DOCUMENTS

| | | | | |
|---|---|---|---|---|
| 5,785,704 | A * | 7/1998 | Bille et al. | 606/17 |
| 5,796,477 | A * | 8/1998 | Teich et al. | 356/318 |
| 5,862,287 | A * | 1/1999 | Stock et al. | 385/123 |
| 6,020,591 | A * | 2/2000 | Harter et al. | 250/458.1 |
| 6,154,310 | A * | 11/2000 | Galvanauskas et al. | 359/328 |
| 6,156,030 | A * | 12/2000 | Neev | 606/10 |
| 6,166,385 | A * | 12/2000 | Webb et al. | 250/458.1 |
| 6,208,886 | B1 * | 3/2001 | Alfano et al. | 600/473 |
| 6,249,630 | B1 * | 6/2001 | Stock et al. | 385/123 |
| 6,325,792 | B1 * | 12/2001 | Swinger et al. | 606/4 |
| 6,351,663 | B1 * | 2/2002 | Flower et al. | 600/476 |
| 6,445,491 | B2 * | 9/2002 | Sucha et al. | 359/330 |
| 6,482,199 | B1 * | 11/2002 | Neev | 606/10 |
| 6,997,923 | B2 * | 2/2006 | Anderson et al. | 606/9 |
| 2001/0045523 | A1 * | 11/2001 | Baer | 250/459.1 |
| 2001/0053878 | A1 * | 12/2001 | Ferris et al. | 600/415 |
| 2002/0034199 | A1 * | 3/2002 | Galvanauskas et al. | 372/22 |
| 2005/0035305 | A1 * | 2/2005 | Kleinfeld et al. | 250/458.1 |

OTHER PUBLICATIONS

Kleinfeld, D., et al., "Two-photon Imaging of Neocortical Microcirculation", *Imaging Neurons: A Laboratory Manual* (R. Yuste, et al., editors), 1999, pp. 23.1-23.15, Cold Spring Harbor Laboratory Press.

Tsai, P., et al., "All-optical, in-situ histology of neuronal tissue with femtosecond laser pulses", *Imaging In Neuroscience and Development: A Laboratory Manual* (R. Yuste, et al., editors), 2005, 102:815-826, Cold Spring Harbor Laboratory Press.

Kleinfeld, D., et al., "Fluctuations and stimulus-induced changes in blood flow observed in individual capillaries in layers 2 through 4 of rat neocortex", *Proc, Natl. Acad. Sci. USA*, Dec. 1998, pp. 15741-15746, vol. 95, Neurobiology.

Fujimoto, J., "Optical coherence tomography for ultrahigh resolution in vivo imaging", *Nature Biotechnology*, vol. 21, No. 11, Nov. 2003, pp. 1361-1367.

Xie, T., et al., "High-speed optical coherence tomography using fiberoptic acousto-optic phase modulation", *Optics Express*, Dec. 1, 2003, pp. 3210-3219, vol. 11, No. 24.

Potter, S., "Vital imaging: Two photons are better than one", *Current Biology* 1996, vol. 6, No. 12:1595-1598.

Iyer, V., et al., "A compact two-photon laser-scanning microscope made from minimally modified commercial components", *Proceedings of SPIE—Multiphoton Microscopy in the Biomedical Sciences II*, A. Periasamy & P.T.C. So, Eds., Jun. 2002, pp. 274-280, vol. 4620.

Mainen, Z. F., et al., "Two-Photon Imaging in Living Brain Slices", *Methods: A Companion to Methods in Enzymology*, 1999, pp. 231-239, vol. 18.

Tsai, P.S. et al., "Principles, Design and Construction of a Two-Photon Laser-Scanning Microscope for In Vitro and In Vivo Brain Imaging", pp. 113-171, Ch. 6 of *In Vivo Optical Imaging of Brain Function*, R.D. Frostig, Ed., 2002, CRC Press.

Tsai, P.S., at al., "All-Optical Histology Using Ultrashort Laser Pulses", *Neuron*, Jul. 3, 2003, pp. 27-41, vol. 39.

* cited by examiner

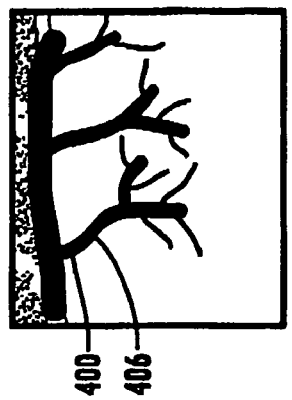
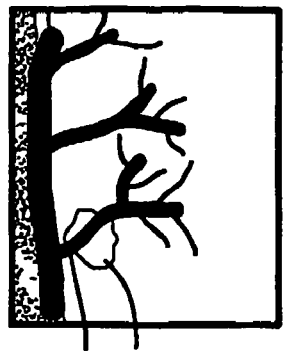
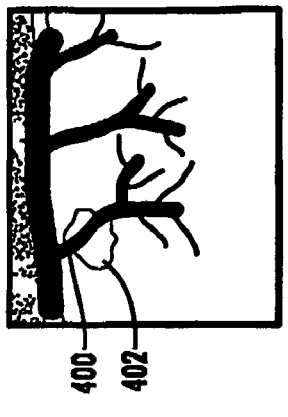
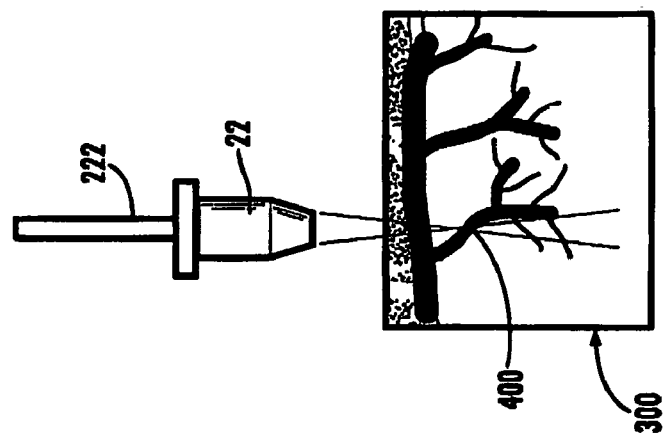
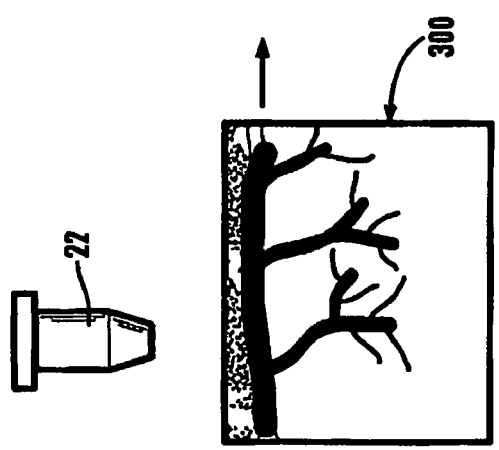

DEVICE AND METHOD FOR INDUCING VASCULAR INJURY AND/OR BLOCKAGE IN AN ANIMAL MODEL

RELATED APPLICATIONS

This application claims the benefit of priority of U.S. Provisional Application Ser. No. 60/432,371 filed Dec. 11, 2002, the disclosure of which is incorporated herein by reference in its entirety.

GOVERNMENT RIGHTS

Pursuant to 35 U.S.C. §202(c), it is hereby acknowledged that the U.S. Government has certain rights in the invention described herein, which was made in part with funds from the National Institute of Neurological Disorders and Stroke, Grants No. R01-NS41096 and No. R01-NS043300-01A1.

FIELD OF THE INVENTION

The present invention relates to a device and method for inducing vascular injury and/or blockage in animal models for the study of vascular disease, and more particularly an optical device and method for producing laser-induced hemorrhage, thrombosis, and breach of the blood-brain barrier in specifically targeted individual blood vessels with micrometer precision.

BACKGROUND OF THE INVENTION

With the average lifespan and age of the population on the increase, vascular diseases are guaranteed to strike growing numbers within the population. Among such diseases are neurovascular disorders, which encompass those conditions that result in cerebrospinal ischemia, infarction, and hemorrhage. To provide an example, every year, over 700,000 people in the United States suffer a stroke, and roughly a quarter of those strokes are fatal. Stroke is therefore the third leading cause of death in the United States. In addition, a large segment of the elderly population is debilitated by dementia. Recently, neuronal vascular disorders, including microstrokes (lacunes), microbleeds, and neurovascular disease have been linked with many forms of dementia, such as Alzheimers's disease and vascular dementia. (Heye and Cervos-Navarro 1996; del Zoppo and Mabuchi 2003; Wardlaw, Sandercock et al. 2003) At present, options for treatment of stroke remain few and of limited efficacy despite years of basic and clinical research. Continued progress in stroke research depends critically on animal models that allow stroke to be studied at various stages, from initial changes in physiological parameters (e.g., blood flow and blood oxygenation) to neuronal death, behavioral impairment, and recovery. (del Zoppo 1998; Lipton 1999; del Zoppo and Mabuchi 2003). Most ischemic stroke models developed to date produce either large-scale injury, or a multitude of small-scale injuries at uncontrolled sites. Most hemorrhagic stroke models developed to date produce either large-scale hemorrhage or systemic injury. These existing models do not allow the production of small-scale, localized injury or blockage to specifically targeted vessels at depth. Such a paradigm is particularly crucial for the study of the effects of ischemic microstrokes and microbleeds.

Existing in vivo animal models of stroke fall into one of five broad categories: 1) occlusion of large vessels by ligation or filament insertion; 2) occlusion of a multitude of microvessels by injection of embolus into the bloodstream; 3) hemorrhagic damage (vessel rupture) by injection of a tissue-degrading substance; 4) model of hemorrhage by injection of whole or fractionated blood; and 5) optically-induced thrombosis of blood vessels by linear absorption of light. There is no reported technique that is capable of producing both thrombotic and hemorrhagic stroke to specific individual vessels deep within the same preparation.

In the case of mechanical occlusion, current techniques involve the blockage of blood flow by a variety of methods. These methods include ligation of large arteries (e.g., carotid artery) (McBean and Kelly 1998)], ligation of smaller arteries (Wei, Rovainen et al. 1995; Wei, Erinjeri et al. 2001), and insertion of a filament into a large artery for the occlusion of a main arterial branch. (e.g., the middle cerebral artery) (Tamura, Graham et al. 1981; Chen, Hsu et al. 1986; Busch, Kruger et al. 1998). Artery ligation results in neuronal injury to large, millimeter or larger sized regions of the rodent brain and is a model for major infarcts.

As a model for microstrokes, microspheres (Lyden and Hedges 1992; Lyden, Zivin et al. 1992; Lyden, Lonzo et al. 1997) or preformed clots (Kudo, Aoyama et al. 1982; Overgaard 1994; Krueger and Busch 2002) can be injected into an artery, leading to occlusion of smaller vessels downstream from the injection site, but without allowing specific individual vessels to be targeted. As a result, physiological changes cannot be correlated to specific local disruptions.

Hemorrhages can be induced by systemic or local injections of agents such as collagenase (Rosenberg, Mun-Bryce et al. 1990)], or tissue plasminogen activator (tPA) (Dijkhuizen, Asahi et al. 2002) to weaken vessels or disrupt the blood-brain barrier. Using such models to evaluate potential treatments is difficult because the effects of these agents can be spread over large, uncontrolled volumes. In addition, the effects of the agent cannot be isolated to the vasculature alone, because the agent can directly affect the surrounding tissue.

Alternatively, direct injection of whole or fractionated blood into the extracellular space has been reported as a model for hemorrhagic stroke (Deinsberger, Vogel et al. 1996; Hickenbottom, Grotta et al. 1999). The spatial localization is limited by diffusion of the injected materials. Additionally, this model is deficient in other aspects of natural hemorrhagic stroke, including the vascular and endothelial response. Current models of hemorrhage cannot be used as models of small hemorrhage, which are necessary for studies of vascular dementia.

For the case of optically-induced thrombosis, previous work utilized green light to excite an intravenously injected photosensitizer. When excited by exposure to light, photosensitizers generate singlet oxygen (Pooler and Valenzeno 1981), which attacks the membranes of the vessel walls (Herrmann, 1983). Damage to the vessel walls then starts a natural cascade of activation that results in the formation of a clot in all exposed vessels (Watson, Dietrich et al. 1985; Krammer 2001). In earlier work, transcranial illumination with diffuse green light exposed blood vessels over a wide lateral and axial extent, 1-3 millimeters in diameter (Watson, Dietrich et al. 1985; Dietrich, Ginsberg et al. 1986; Dietrich, Ginsberg et al. 1986).

More recently, work has been done using green light that is tightly focused through a microscope objective, constraining the lateral dimension of exposure at the focal plane to approximately one micrometer (Schaffer, Ebner et al. 2003; Schaffer, Ebner et al. 2003; Schaffer, Tsai et al. 2003), allowing individual vessels to be clotted. While very powerful, this focal photothrombotic stroke model has one major drawback: localized clotting can be achieved only in surface vessels. This limitation is due to the single-photon excitation of the photosensitizer molecule. When focused on a deep-lying vessel to induce a clot, all vasculature lying above that vessel is also clotted, preventing the use of this model for studying the effect of localized thrombosis in individual vessels at depth.

Alternatively, highly absorbed wavelengths of light (e.g., 10.2 microns from a $CO_2$ laser) are used extensively in neurosurgery to simultaneously remove neuronal and vascular tissue while concurrently cauterizing the remaining portions of the removed blood vessels. The mechanism of damage relies on the linear absorption of the laser light by water and other tissue constituents and, therefore, does not require the presence of an exogenous photosensitizer. The high absorption coefficient of the tissue at these wavelengths results in substantial energy absorption and thermal buildup within the targeted tissue. The concurrent thermal diffusion out of the targeted volume results in an extended region of collateral thermal damage.

Current medical treatment for stroke requires therapeutic intervention within hours of the stroke to be optimally effective. Full understanding of the mechanisms and efficacy of these interventions therefore requires real-time visualization of stroke with high spatial and temporal resolution. Previously, real-time visualization and quantification of the effects of vascular damage on blood flow and blood vessel morphology have been performed using technologies, such as laser Doppler flowmetry (Dirnagl, Kaplan et al. 1989; Nakase, Kakizaki et al. 1995), magnetic resonance imaging (MRI) (Hoehn-Berlage, Norris et al. 1995; Busch, Kruger et al. 1998), positron emission tomography (PET) (Marchal, Young et al. 1999), computer-aided tomography (CAT), fluorescent video microscopy (Wei, Rovainen et al. 1995; Wei, Erinjeri et al. 2001; Ishikawa, Sekizuka et al. 2002), or confocal laser scanning microscopy (Seylaz, Charbonne et al. 1999; Pinard, Nallet et al. 2002). With the exception of the light microscopy, these techniques are limited to determining average blood flow over 100-1000-micrometer-sized areas. While such averages may be relevant for determining the degree of ischemia or hemorrhage, they provide no input on changes in flow and morphology in individual vessels, save for the largest branches of the cerebral vasculature. Fluorescent video microscopy allows individual vessels to be studied, but is limited to the observation of surface vessels only, while confocal microscopy allows vessels up to approximately 50 μm beneath the surface to be visualized. These observation techniques have allowed quantitative characterization of changes in blood flow velocity and blood vessel dilation as a result of large-scale ischemia produced by surgical occlusion of arteries and arterioles (Wei, Rovainen et al. 1995; Wei, Craven et al. 1998; Seylaz, Charbonne et al. 1999; Wei, Erinjeri et al. 2001; Pinard, Nallet et al. 2002). These studies could not, however, address local changes in blood flow and vessels near an isolated occlusion. Recently, fluorescent video microscopy was used to study vessel dilation after photochemically-induced clots in individual arterioles, but the results were limited to surface vessels and blood flow could not be resolved (Ishikawa, Sekizuka et al. 2002).

Another modality of analysis for current models of induced stroke is based on the observation of behavior deficits in the subject and post-mortem histology of the targeted and collateral tissue regions. These widely utilized methods are performed hours to days after the onset of damage and, therefore, are unable to elucidate the dynamics and mechanisms involved in the propagation of injury due to vascular damage.

The study of microstrokes and microhemorrhages requires microscopic resolution, coupled with the ability to either precisely target or locate the microscopic vascular disturbance within the brain volume. Using nonlinear microscopy, local changes in blood flow due to isolated occlusions can be studied and quantified in real-time.

The use of nonlinear optical effects to provide contrast for image formation has revolutionized microscopy over the past decade. Many nonlinear effects are now used for imaging, including second- and third-harmonic generation, Coherent Anti-Stokes Raman scattering, the Kerr effect, and multi-photon excited fluorescence.

One non-linear technique is two-photon laser scanning microscopy, or "TPLSM" (Denk, Strickler et al. 1990; Denk 1994), which allows fluorescence imaging with intrinsic optical sectioning deep inside scattering specimens with diffraction-limited resolution. Briefly, an ultrashort laser pulse is tightly focused inside a specimen tagged with a fluorescent molecule that does not linearly absorb at the wavelength of the ultrashort laser. At the laser focus, the laser intensity can become high enough to induce two-photon excitation of the fluorescent molecule. Because the excitation is nonlinear, this fluorescence is only produced in the focal volume where the laser intensity is high. The fluorescence intensity is then recorded as the position of the laser focus is scanned throughout the specimen forming a three-dimensional image. In addition, because photoexcitation occurs only at the laser focus, there is significantly reduced bleaching of fluorescent dyes and photodamage to the sample as compared to linear imaging techniques.

TPLSM is especially well suited to in vivo imaging deep into highly scattering specimens, such as brain. In widefield or confocal fluorescence microscopy, the fluorescence must be imaged to a camera or to a pinhole, respectively. Scattering of the fluorescence leads to an unwanted background in widefield microscopy and to decreased signal strength in confocal microscopy. In TPLSM, however, because all the fluorescence originates from the focal volume, it need only be detected in order to contribute to the signal, not imaged. Thus fluorescence that is scattered on the way to the detector still contributes to image formation, and does not produce unwanted background. This immunity to scattering of the fluorescence allows imaging deep into scattering samples. The imaging depth is ultimately limited by scattering of the ultrashort laser beam. In practice, one can image up to 500 micrometer beneath the cortical surface in rat (providing access to layers 1-4 of the cortex), without loss of image resolution. For neuronal tissue with labeling throughout the tissue, a theoretical limit for imaging depth is approximately 1 millimeter.

TPLSM further provides means for measuring and quantifying the velocity, i.e., direction and speed, and flux of red blood cell (RBC) movement and plasma flow in vivo under acute as well as chronic conditions. These measurements make use of either fluorescently labeled plasma, in which case cells in the blood, such as RBCs and leukocytes, appear as dark objects on a bright background, or the use of fluorescently labeled RBCs.

The above-described technologies provide means for forming and observing strokes. However, these techniques for induction of stroke are incapable of producing hemorrhage, thrombosis, and breach of the blood-brain barrier targeted to specific individual blood vessels. Further, no technique is currently available for the production of surface or subsurface vascular injury localized with micrometer precision, thereby permitting the disruption of the smallest vessels, i.e., capillaries. Accordingly, the need remains for a device and method with such capabilities.

SUMMARY OF INVENTION

The present invention provides a device and method for optically inducing precision vascular injury and/or blockage deep in the tissue of an animal. No exogenous agents are required to facilitate the injury, as the laser light interacts directly with the endogenous tissue and fluids. In an exemplary embodiment, a tightly focused beam of high intensity, ultrashort, laser pulses drives nonlinear interactions between the laser light and the tissue at the focus of the beam, producing photodisruption at the targeted vasculature. These nonlinear interactions result in both direct photoionization of the tissue at the focus and thermoelastic damage to the local surrounding tissue. As a result of these damage mechanisms, a localized hemorrhage, thrombosis, or breach of the blood-brain barrier is formed within a single targeted vessel, providing an in vivo animal model for vascular injury or blockage. Because of the nonlinear nature of the laser-tissue interaction, photodisruption can be targeted deep to the surface of the tissue without extensive collateral damage to tissue surrounding the targeted vessel.

According to the inventive method for production and observation of localized photodisruption, optical access to vasculature of the peripheral and central nervous system is obtained through a window. For the case of brain vasculature, an optically transparent cranial window consisting of either a coverslip-sealed craniotomy, a thinned-skull preparation, or an intrinsically thin skull is utilized. In the preferred embodiment, an intravenous injection of fluorescent water-soluble tracer is used to visualize target vessels and quantify the blood flow through the cranial window. In the preferred embodiment, two-photon laser scanning microscopy (TPLSM) is used, however, other observation procedures may also be used.

According to the present invention, ultrashort laser pulses are used to induce photodisruptive breakdown in vasculature thereby controllably producing hemorrhage, thrombosis, as well as breach of the blood-brain barrier in individual, specifically targeted blood vessels. Ultrashort laser pulses of lower energy are also used to image and quantify the baseline and altered states of blood flow. Such analysis provide a real-time, in vivo model for the dynamics and effects of vascular injury, such as occurs in stroke. Breakdown is produced in individually targeted vessels with approximately 100 to 10000 nanojoule pulses. Induced thrombi are found to be stable past 6 hours. Thrombosis has been demonstrated in vessels ranging in diameter from 5 to 50 micrometers. Hemorrhagic damage has been demonstrated in vessels ranging in diameter from 5 to 1000 micrometers. Three-dimensional localization of damage has been demonstrated by optical sections that were taken before and after the vascular damage has been induced, and from histological sections of post-mortem tissue. In both cases the sections spans the entire three-dimensional volume of interest. Blood vessels neighboring the targeted vessel showed no signs of vascular damage, including vessels directly above and directly below the targeted vessel.

The inventive device and method are not limited to applications for modeling of stroke or other vascular injury of the brain, but can be used for the study of vascular disease in other organs, including, but not limited to heart, liver and kidney. In general, any disease involving disruption of normal vascular function can be modeled and studied using the device and method of the present invention.

BRIEF DESCRIPTION OF THE DRAWINGS

The invention, both as to its organization and manner of operation may be further understood by reference to the following description taken in conjunction with the following drawings wherein:

FIGS. 4a and 4b are diagrammatic views of a cross-section of tissue before and during exposure to photodisruption, respectively. FIGS. 4c, 4d, and 4e are diagrammatic views of the tissue showing a hemorrhage, a breach of the blood-brain barrier, and a thrombosis, respectively, induced by photodisruption.

DETAILED DESCRIPTION OF PREFERRED EMBODIMENTS

The following detailed description provides examples of application of the device and method of the invention to modeling of stroke or other vascular injury in the brain. These examples are not intended to be limiting. Applications of the invention go beyond those relating to simulation and study of stroke, extending to the study of vascular disease in other organs, including, but not limited to, heart, liver and kidney, and other areas of the body, for conditions such as peripheral vascular disease.

Nonlinear optical induction of vascular injury and/or blockage is performed using high intensity, ultrashort laser pulses. Nonlinear microscopy is used to monitor and quantify changes of physiological parameters (e.g., blood flow, or blood oxygenation) in real-time.

Photodisruption relies on nonlinear interaction between the laser light and endogenous tissue constituents to generate either thrombosis, breach of the blood-brain barrier resulting in extravasation of blood plasma but not red blood cells, or hemorrhage resulting in extravasation of both blood plasma and red blood cells. This method does not require the presence of an exogenous photosensitizer. Use of laser wavelengths that are neither highly scattered nor highly absorbed by the tissue allow for both imaging and photodisruption to be targeted deep to the tissue surface, localized in three dimensions, and performed with negligible thermal damage to the surrounding tissue. Photodisruption is instigated by multiphoton and avalanche ionization. The resulting damage is from either direct vaporization, if the tissue is located in the focal volume where the laser energy is nonlinearly absorbed, or mechanical disruption by either a shock wave or cavitation bubble. By locating the laser focus at different positions inside or on the vessel wall, a variety of vascular injuries can be produced. When the laser pulse is focused on the wall of a vessel, the cells comprising the wall are vaporized, producing a hemorrhage. When the laser pulse is focused into the lumen of the vessel, the vessel wall is most likely damaged by the shock wave, potentially triggering the clotting cascade and formation of a thrombus, and/or leading to hemorrhage or breach of the blood-brain barrier.

In the preferred embodiment, targeting of vessels, as well as imaging and quantification of physiological parameters are performed by TPLSM. Other techniques for observation of the effects of photodisruption, which may be used in lieu of or in combination with TPLSM include optical coherence tomography (OCT), magnetic resonance imaging (MRI), functional magnetic resonance imaging, multi-spectral intrinsic imaging, positron emission tomography (PET), time resolved light scattering, Doppler flowmetry, and surface imaging of blood vessels with wide-field videography.

Figure 1:
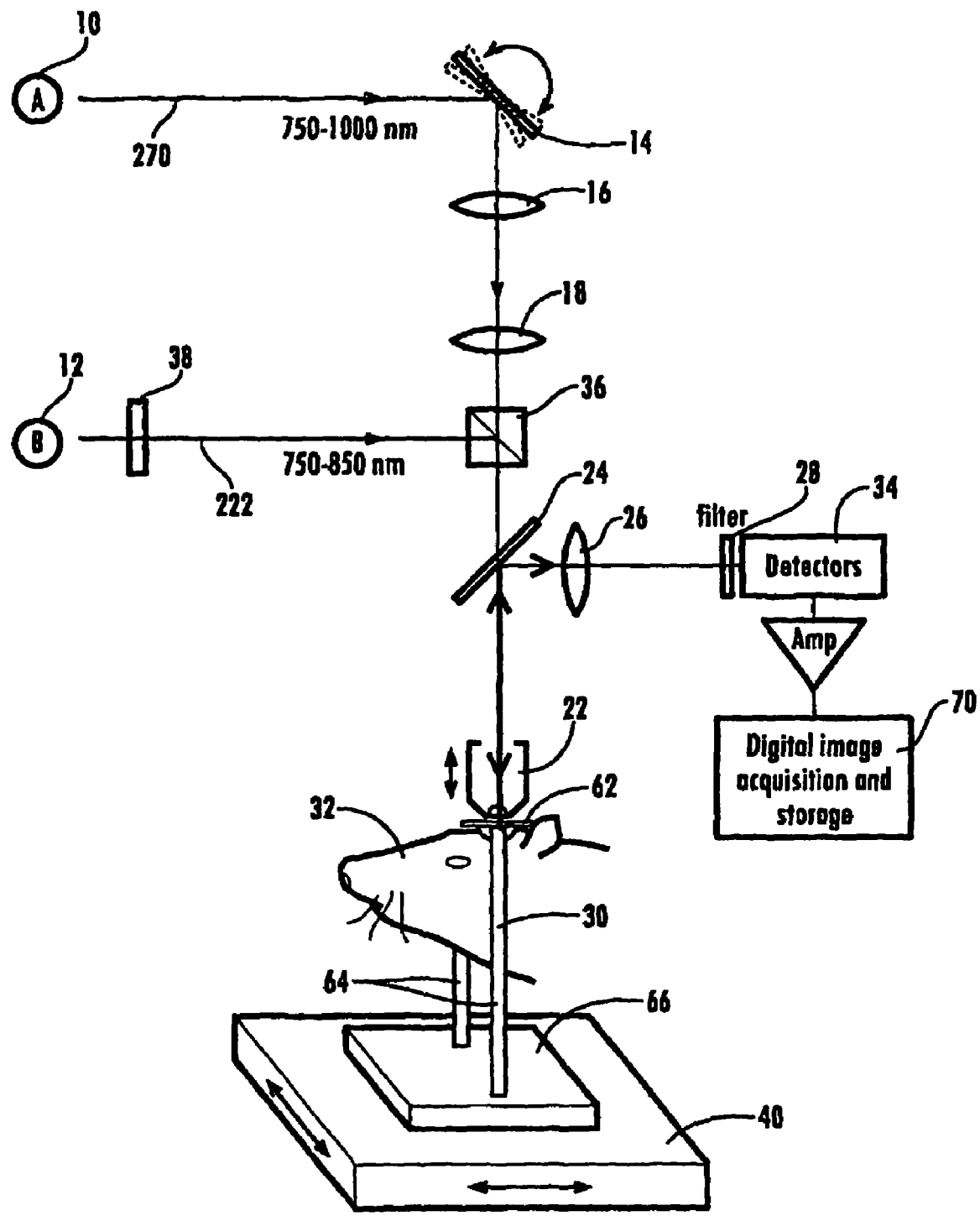
FIG. 1 is a schematic diagram of an exemplary arrangement for the optics and optomechanics of the inventive device, including scan optics, detectors, and sample stage.

The major optics and optomechanics of the modified two photon laser scanning microscope are illustrated in FIG. 1. As illustrated, the device broadly includes multiple laser source/electro-optics assemblies 10 and 12, a modified two-photon laser scanning microscope 20, and an animal preparation mount 30 attached to a translation stage 40. The laser sources for the two beams of laser pulses have pulse parameters appropriate for nonlinear imaging and photodisruption, respectively. In the preferred embodiment, the first source assembly 10 is capable of producing roughly 100 femtosecond, 720 to 900 nanometer laser pulses with energies of up to approximately 10 nanojoules at a repetition rate of 76 megahertz for the purpose of nonlinear microscopy. A second source assembly 12 is capable of producing roughly 100 femtosecond, 800 nanometer laser pulses with energies of up to approximately 1 millijoule at a repetition rate of 1 kilohertz. Alternatively, the laser sources can be any other laser systems or combinations of systems appropriate for nonlinear microscopy and photodisruption, respectively. The two-photon laser scanning microscope 20 is adapted for concurrent delivery of a second beam line for photodisruption. The animal preparation mount 30 is designed to stably hold the animal preparation 32 for optical access to the vasculature. A translation stage 40 and kinematic mount allow positioning to micrometer accuracy. Auxiliary equipment can be included for monitoring and maintaining homeostatic conditions for the animal preparation.

Figure 2:
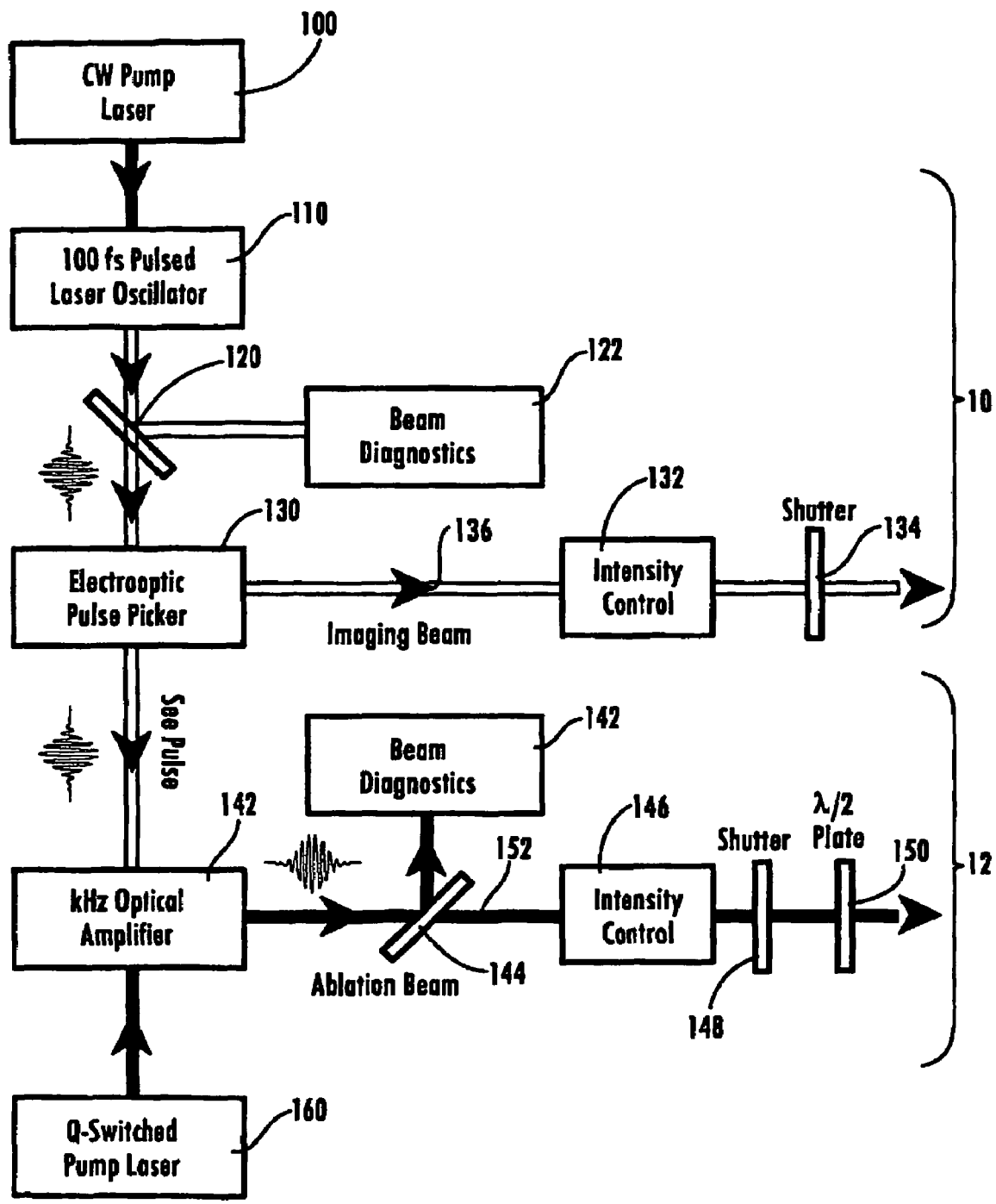
FIG. 2 is a schematic diagram of laser sources for a first embodiment of the device, wherein two coupled laser sources are used for imaging and photodisruption.

Referring to FIG. 2, in a first embodiment, the laser source for TPLSM and the laser source for photodisruption are separate but coupled laser sources. In this first exemplary embodiment, laser oscillator 110 is a Titanium: sapphire (Ti: sapphire) laser with a pulse width of approximately 100 femtoseconds. For purposes of the present invention, pulse widths may fall in the range of around 10 femtoseconds to the 100 picoseconds. Appropriate lasers are commercially available, for example, under the trademark Mira® 900 (Coherent, Inc., Santa Clara, Calif.). Laser oscillator 110 is used both as the imaging source for a modified two-photon laser scanning microscope, and as a seed for a multi-pass optical amplifier 140 through a electrooptic pulse picker 130. An example of an appropriate amplifier for use in the inventive device is that of Kapteyn and Murnane (Backus, Bartels et al. 2001). Such systems, producing pulses with a duration of approximately 100 femtoseconds and energies up to approximately 1 millijoule at a repetition rate of approximately 1 kilohertz, are commercially available, for example, under the trademark Hurricane™ (Positive Light, Inc., Los Gatos, Calif.). The amplified beam from the multi-pass optical amplifier serves as a photodisruption beam for vascular injury. The pump laser 100 for the laser oscillator is a continuous wave (CW) solid state laser, such as the 10 W Verdi-V10 laser available from Coherent, Inc. The pump laser 160 for the optical amplifier 140 is a pulsed solid state laser. Beam diagnostics 122, 142 include a power meter, spectrometer, and autocorrelator, which receive light from the optical oscillator or amplifier via beamsplitters 120, 144. Intensity controls 132, 146 and mechanical shutters 134, 148 are provided independently for each beam path 136, 152. A half-wave plate 150 is placed in the photodisruption beam path 152 to rotate the polarization of the beam for effective polarization mixing with the oscillator (imaging) beam 152 in the modified microscope.

Figure 3:
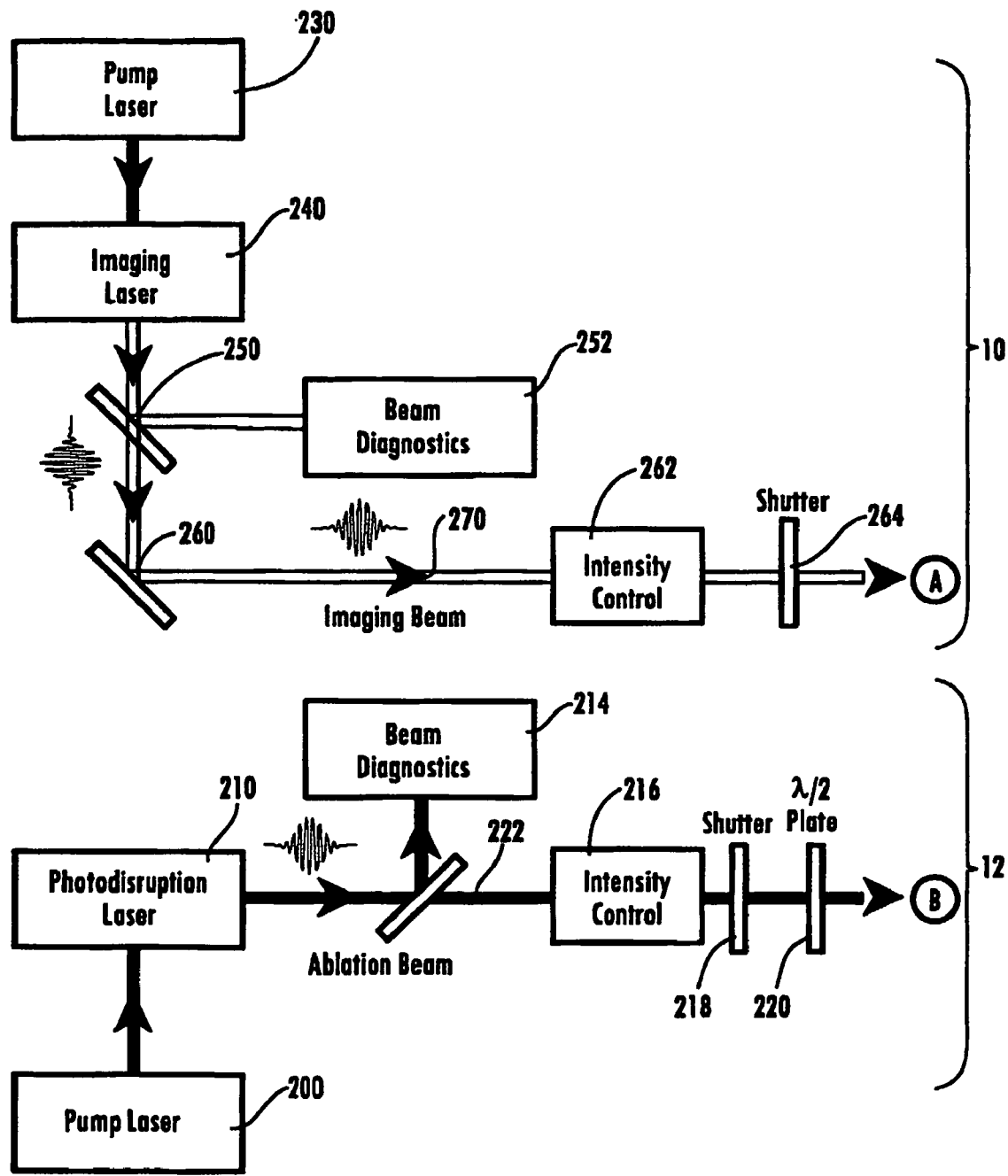
FIG. 3 is a schematic diagram of laser sources for a second embodiment of the device, wherein two separate laser sources are used for imaging and photodisruption.

In a second embodiment, a separate laser source assembly can be used for each of TPLSM and photodisruption of subsurface vessels, as illustrated in FIG. 3. In this alternative embodiment, the first laser/electrooptics assembly 10 includes a photodisruption laser 210 pumped by a separate pump laser 200 to produce the ablation beam 222 of high energy pulses with or without the use of an optical amplifier. As in the first embodiment, beamsplitter 212 diverts a portion of the beam 222 to beam diagnostics 214, which includes a power meter, spectrometer, and autocorrelator. Intensity control 216 and mechanical shutter 218 are provided in the beam path 222. A half-wave plate 220 is placed in the beam path 152 to rotate the polarization of the beam for effective polarization mixing with the imaging beam 270 in the modified microscope.

In the separate, second laser/electrooptics assembly 12, imaging beam 270 is produced in a similar manner to that of oscillating beam 136 of the first embodiment. Imaging laser 240 is pumped by laser 230. Beam diagnostics 252 receives light from the imaging laser 240 via beamsplitter 250. Intensity control 262 and mechanical shutter 264 are provided in beam path 270. A half-wave plate 150 is placed in the amplified beam path 152 to rotate the polarization of the beam for effective polarization mixing with the oscillator (imaging) beam 152 in the modified microscope.

Referring again to FIG. 1, the modified two photon laser scanning microscope includes a pair of scan mirrors 14 together with a scan lens 16, a tube lens 18, and an objective 22, which together serve to raster the oscillator beam across the animal preparation 32 for imaging. The objective 22 has a high numerical aperture (NA) in the range from 0.1 to 1.3 NA, which is typically available with standard water-immersion objectives. The choice of the numerical aperture is based on considerations that tie the NA of the microscope objective 22 to the working distance, laser penetration depth and resolution at a given location of tissue. The amplified ultrashort pulses for photodisruption (from source 12) are combined into a common optical path with the imaging beam by polarizing beamsplitter 36.

The detection optics comprise a dichroic mirror 24, a mixture of colored glass and interference filters 28, collection lens 26, and detectors 34, all receiving photons from the animal preparation 32 through the objective lens 22. A digital image acquisition and storage system 70 is provided to store sections in the form of digital images. Such a system 70 comprises a computer system and suitable acquisition software and imaging software to visualize and quantify the blood flow in the animal preparation. Additional software and/or hardware can be included to provide positioning control and coordination of the translation stage 40, allowing precise positioning and assignment of reference coordinates to the stored images. Additional optics can be easily inserted for simultaneous detection and discrimination in multiple wavelength bands.

In the preferred embodiment, targeting of specific vessels and visualization of blood flow can be performed by two-photon laser scanning microscopy at multiple adjacent fields of view. Then, the animal can be removed and precisely repositioned in the apparatus using a kinematic mount for observation using, in one preferred embodiment, optical coherence tomography (OCT), a technique developed in the early 1990s which enables non-invasive, high resolution in vivo imaging in turbid biological tissue (see, e.g., Fujimoto, 2003). Additional or alternative observation and vessel targeting modalities may be used, including magnetic resonance imaging (MRI), functional magnetic resonance imaging, multi-spectral intrinsic imaging, positron emission tomography, time resolved light scattering, Doppler flowmetry, or surface imaging of blood vessels with wide-field videography. As an alternative to repositioning, the animal can remain in a fixed position and the instrumentation moved into position for viewing. In this latter embodiment, the TPLSM assembly would be mounted on an appropriate translation stage or platform in a system that includes one or more additional types of observation instrumentation. The second instrument, also mounted on a stable translation stage, can be positioned for observing the animal.

The head-fixed mount 30 is constructed from a metal plate 62 which is directly attached to the animal preparation 32. The metal plate 62 is mounted onto metal rods 64 which attach to a kinematic baseplate 66 that can be removed and replaced with high precision. The kinematic base plate 66 attaches to a translation stage 40 that can be connected to system controller 70 to provide computer control to deliver micrometer position accuracy.

Additional details of the components of the TPLSM and examples of commercial sources for the components of the TPLSM are provided in Chapter 6 ("Principles, Design and Construction of a Two-Photon Laser-Scanning Microscope for In Vitro and In Vivo Brain Imaging", by P. S. Tsai, et al.) of *In Vivo Optical Imaging of Brain Function*, ed. Ron D. Frostig, 2002, CRC Press, pp. 113-171, which is incorporated herein by reference.

For practicing the method of the present invention, mode-locked laser 10 produces a train of ultrashort laser pulses capable of being focused to peak intensities exceeding approximately $10^{10}$ W/cm$^2$ appropriate for nonlinear microscopy. This train of pulses is directed to laser scanning microscope 20 and focused at the animal preparation 32 for the purpose of monitoring physiological parameters, such as blood flow, blood oxygenation, or cellular physiology. A subset of the pulses is diverted by pulse picker 130 to optical amplifier 140 to produce ultrashort laser pulses capable of being focused to peak intensities exceeding approximately $10^{13}$ W/cm$^2$ as appropriate for photodisruption. This beam of amplified pulses is also focused at the animal preparation 32 for the purpose of producing photodisruption by nonlinear interaction with the endogenous tissue constituents. Due to the high-order dependence of these nonlinear interactions on laser intensity, the probability of interaction is negligible everywhere except in the immediate vicinity of the focus of the laser beam. Sub-femtoliter focal volumes can be achieved, resulting in localization of vascular damage down to a single specific blood vessel, and imaging with sub-micrometer resolution.

Three categories of vascular injury—thrombosis, breach of the blood-brain and hemorrhage—can be selectively produced by optimization of three parameters: the pulse energy, the number of pulses applied, and the targeting location within the vessel. Targeting the pulses to the vessel wall results in direct photoionization of the cells comprising the vasculature. Targeting the pulses to the vessel lumen results in photoionization of the fluid within the lumen, leading to a cavitation bubble and a shock wave which propagates to the vessel wall, and causes injury. The injury resulting from these mechanisms may be severe enough to degrade the blood-brain barrier, trigger a natural clotting cascade, or rupture the vessel. Because the amplitude of produced shock waves falls off rapidly with propagation distance, collateral damage to surrounding tissue is minimal.

An animal is prepared for optical access to neuronal vasculature by performing a craniotomy and sealing the opening with a coverslip and 1% agarose in artificial cerebral spinal fluid (ACSF). Small openings were left around one or more edges of the coverslip to permit insertion of small electrical probes to contact or penetrate the brain tissue for the purpose of electrical stimulation and/or recording (Svoboda, Denk et al. 1997). The animal was then placed into a head-fixed mount 30 at the base of the apparatus. Alternatively, optical tracking (e.g, using fiber laser delivery), can be used for animal preparations that are not fixed to a stationary mount. Auxiliary equipment may be provided at the animal preparation to monitor and maintain homeostatic conditions, as well as provide sensory stimulation.

Fluorescent labeling of the blood plasma allows targeting of the vessels as well as observation of blood flow using TPLSM. The blood plasma is labeled by intravenous injection of a water-soluble fluorescent tracer. Blood flow is visualized by monitoring the motion of erythrocytes or other blood stream constituents, which appear as dark objects moving against a fluorescent blood plasma background. Imaging of the neuronal blood flow is performed and maps of the vascular connectivity are generated with micrometer resolution.

Quantified maps of blood flow are generated by analysis of the collected images. Quantitative blood flow analysis consists of calculating the streak angle of contrast-generating objects in the bloodstream visualized by TPLSM. Alternatively, two-point correlation of intensity changes along the length of the imaged vessel can be used to quantify the blood flow.

Vascular damage is induced in a subpopulation of the mapped blood vessels by tightly focusing a controlled number of photodisruptive laser pulses in those blood vessels. Either hemorrhage, thrombosis, or breach of the blood-brain barrier can be produced without requiring the presence of an exogenous photosensitizer in the blood stream. Additionally, multiple types of vascular injury can be induced to different targets within the same animal preparation. After vascular injury has been induced, more imaging of neuronal blood flow is performed, and changes in blood flow are quantified. Further, any other physiological parameter amenable to fluorescence microscopy can also be observed with TPLSM, e.g., intracellular $Ca^{2+}$ concentration, Reduced Nicotinamide Adenine Dinucleotide/Nicotinamide Adenine Dinucleotide (NADH/NAD$^+$) ratio, or the transmembrane voltage. Post-operative observations are used to correlate the induced vascular injury and real-time observed physiological changes to behavioral deficits or post-mortem histology.

FIGS. 4a and 4b provide simulated images of a cross-section of tissue 300 before and during exposure to the photodisruptive pulses, respectively. Microscope objective lens 22 is positioned over the desired target area for irradiation on the animal by movement of one or both of the kinematic mount 66 and translation stage 40. In FIG. 4b, the photodisruption beam 222 is focused by objective lens 22 onto target vasculature 400. FIGS. 4c, 4d, and 4e are images of the tissue showing a hemorrhage 402, a breach of the blood-brain barrier 404, and a thrombosis 406, respectively, all of which were induced by photodisruption.

EXAMPLE 1

Sprague-Dawley rats, 100-300 grams in weight, were prepared in order to provide optical access to neuronal blood flow. The animals were anesthetized with urethane and craniotomies, roughly 4 millimeters by 4 millimeters in extent, were performed over parietal cortex to create a cranial window. The dura was removed and a metal frame 62 was glued to the skull. The exposed brain surface was covered with 1.0 to 1.5% low gelling temperature agarose (W/V) in artificial cerebral spinal fluid (ACSF). A glass coverslip was clipped in place on top of the agarose to maintain pressure over the brain and to provide optical access. Water soluble fluorescein-isothiocyanate dextran was injected intravenously to label the blood plasma for the purpose of targeting and imaging vessels. Alternatively, a thinned-skull preparation can be performed to gain optical access to the neuronal blood flow. The metal frame is then mounted to a kinematic mount and computer-controlled translation stage at the base of the apparatus via metal rods. Homeostatic conditions are monitored and maintained by auxiliary equipment at the base of the apparatus, including, thermometer, heat blanket, oxygenated gas flow, electrocardiogram, and blood pressure monitor. Additional auxiliary equipment (e.g., mechanical whisker stimulator) at the base allows for sensory stimulation during the course of the experiments.

TPLSM was used to visualize vessels and select a target for photodisruption. Alternative means for labeling include the injection of fluorescently-labeled erythrocytes, microscopic exogenous fluorescent probes or addition of a stain to the blood stream that localizes to endogenous cellular components. For observation of the vessel walls, a lipophilic stain can be used for labeling.

Once a target has been selected, a stack of TPLSM optical sections was taken, spanning the area around the target from the surface to roughly 300 micrometers below the surface to visualize the three-dimensional organization of regional blood vessels. Multiple adjacent image stacks can be taken to extend the field of observation. A rapid time series of line scans were taken of a target blood vessel as well as surrounding blood vessels for quantification (measurement of velocity, flux and mass flux) of blood flow, as discussed further below.

To initiate vascular disruption, a 1-kilohertz train of laser pulses of roughly 100-femtosecond pulsewidth with a wavelength of 800-nanometers were focused into the lumen of the vessel or at the surface of the vessel while continuously monitoring with TPLSM. After a train of approximately 10 laser pulses, the irradiated area was observed for any vascular changes. The laser pulse energy started at ~50 nanojoules. If no vascular changes were observed, the laser power was increased and irradiation repeated. Vascular disruption occurred at energies of around ~0.3 microjoules.

The morphology of vessels can be monitored at a frame rate of up of several hertz, while the flow velocity in vessels can be monitored at kHz rates by scanning only a single line along the length of the vessel. In some cases, velocity of RBCs was measured in the target and surrounding vessels. To measure RBC velocity in a single vessel with TPLSM, the imaging laser is scanned repeatedly along the length of a vessel. This line-scan results in a space-time image, in which the motion of the RBCs through the vessel is recorded as dark streaks. Using the time between successive linescans and length of each line-scan, the velocity of the RBC can be computed by an automated process.

At the end of the imaging experiments (5 to 6 hours post-clot formation), the animal is administered an overdose of Nembutal and transcardially perfused with phosphate buffered saline (PBS) followed by 4% paraformaldehyde (W/V) in PBS. The brain is removed and equilibrated with solution of 30% sucrose(W/V) in PBS. The brain is sectioned (50 micrometer thick sections) on a freezing, sliding microtome and serially collected in PBS with 0.2% azide (W/V).

The expression of cFOS by immunolocalization has been linked to cell stress and damage associated with ischemia and also with exposure to ultraviolet laser radiation. Control experiments were performed to eliminate the possibility of cFOS upregulation in response to the surgical preparation or two-photon imaging process. In these control experiments, cFOS immunostaining was only scattered and sparse. Next, the induction of cFOS expression was used as an indicator of cell stress in response to photodisruptively induced vessel injury or blockage. In contrast to the control experiments, cFOS upregulation is induced by local photodisruption of blood flow in the vicinity of targeted vessels. This provides corroborative evidence for downstream ischemic cellular pathology following photodisruption-induced injury to blood vessels.

Additionally, immunodetection of infused fluorescein reveals sites of blood-brain barrier breach. The large molecular size of the intravenously injected dye (2 megadalton fluorescein-isothiocyanate dextran) resulted in exclusion of dye from most of the brain parenchyma. Sections stained with anti-fluorescein antibody demonstrated only restricted sites with marked parenchymal labeling within several hundred micrometers of the cortical surface. This staining outlined neurons and in some cases appeared to also be incorporated where plasma extravasation was visualized in vivo during photodisruptive production of hemorrhage or breach of the blood-brain barrier.

EXAMPLE 2

Using the experimental set-up (animal preparation, system configuration and measurement) described in Example 1, photodisruption was performed on vessels in the cortex ranging in depth from the surface to ~175 micrometers in depth. The resulting vascular disruption was found to divide into three categories, which are listed below in order of the approximate severity and size of the damage to the microvessel:

Thrombosis—Near the threshold energy for vascular disruption and with a limited number of pulses, photodisruption results in extremely limited extravasation of plasma. TPSLM images were taken at various time points before, during and after vascular photodisruption. In an exemplary experiment, the vessel is intact before irradiation. After irradiation with 10 pulses of 0.3 microjoules, a small amount of extravasated plasma could be visualized as fluorescence outside the vessel walls, however, the vessel lumen remained unobstructed. Extravasated fluorescence continued to spread for several seconds after irradiation, but remained spatially confined to within 5 micrometers of the vessel. After a second irradiation with 10 pulses at 0.3 microjoules, thrombosis began within several seconds. In the targeted vessel, unmoving, dark areas indicated the coalescence of RBCs and perhaps platelets. Bright stationary areas indicate plasma within the vessel that may be stagnant and without RBCs. A clot that was formed was observed to be stable for the entire period of observation (2 hours).

Breach of the Blood-Brain Barrier—Following photodisruption, a weakening of the blood-brain barrier can allow the extravasation of fluorescein-labeled plasma to fill a volume around the targeted vessel. Penetration of the plasma into the extra-vascular space was not necessarily limited to regions immediately adjacent to the target vessel. In exemplary experiments, fluorescent dye penetrates the parenchyma up to ~30 micrometers radially from the target vessel. In some instances, leakage through the blood-brain barrier was accompanied by the formation of a thombotic clot within the vessel. In other cases, blood flow remained unobstructed within the target vessel throughout irradiation, extravasation and subsequent observation. RBC velocity remained unchanged by the irradiation and subsequent vessel leakage.

Hemorrhage—Greater laser energies and/or increased numbers of pulses, lead to a larger disruption of the targeted vessel. In an exemplary experiment, a microvessel 125 micrometers below the cortical surface was observed before and after irradiation with 10 pulses of 1 microjoule energy. Initial fluorescein leakage was rapid, reaching a diameter of 60 micrometer within 1 second. The plasma continued to expand, stabilizing to a volume of about 0.002 $mm^3$. In addition to fluorescently labeled plasma, RBCs were pushed into the parenchyma and were visualized with white light microscopy immediately after photodisruption.

Ultrashort laser-induced photodisruption comprises electron-ion plasma, shock wave, and cavitation bubble formation, as described above. Vascular disruption can be caused by any one of these optically-triggered events. It is believed that when the laser is focused directly on the vessel wall, ionization removes portions of the endothelial cell. When the laser is focused into the vessel lumen, ionization occurs in blood plasma, or perhaps in a passing red blood cell. In this case, the vessel walls are likely not directly affected by the ionization because the ionization volume is small relative to the vessel lumen, and the products of ionization are swept downstream by the flowing blood. However, the shock wave and the cavitation bubble that follow optical breakdown may locally disrupt endothelial cells. The size and strength of the shock wave and cavitation bubble depend on the total amount of laser energy, so that the extent of injury to the vasculature and the tissue can be modulated by the laser power and number of applied pulses.

At low energies, near the threshold for vascular disruption, a weak shockwave and small cavitation bubble transiently injure the endothelial cells. The injury may be severe enough to degrade the blood-brain barrier, allowing the observed extravasation of fluorescein-labeled plasma, but the leakage is transient. The injury to the endothelial cells may be sufficiently mild that the cells recover, or the endogenous clotting cascade may seal the breach quickly. In some cases, the injury can also trigger thrombosis that completely blocks the vessel, but in other cases, the lumen remains unobstructed.

At higher laser energies, the shockwave may induce sufficient damage to the endothelial cells to disrupt the blood-brain barrier for longer times and over larger areas, allowing bodies such as RBCs to invade the parenchyma. At even higher energies, the shockwave is sufficiently strong that it can completely rupture the vessel and possibly induce direct damage to the tissue surrounding the vessels. These larger vascular disruptions result in a hemorrhage that develops into an intra-parenchymal hematoma, a clotted mass that includes RBCs. It may be noted that even these larger vascular hemorrhages are still three-dimensionally localized, as tissue surrounding the hemorrhage is not disrupted. This tissue immediately bordering the vascular injuries will be at the greatest risk for infarction and consequently, the most interesting to study.

Extravascular tissue remains relatively unaffected by the photodisruption in the vessel for several reasons. Because only a small amount of total energy is delivered by the laser, collateral damage by thermal mechanisms is insignificant. The ionization plasma is confined to volume less than 1 micrometer in diameter. The pressure induced by the shockwaves falls off with increasing distance, thereby limiting the total volume affected by the shock. With appropriate selection of energy, this volume is comprised mostly of the vessel lumen and the endothelial cells. Vascular cells and tissue which wrap completely around the target vessel, e.g., endothelial cells and basement membrane, are preferentially affected by the photodisruption when compared to cells which simply abut the vessel. Because vascular cells wrap around the source of the shockwave, the pressure wave translates into tensile stress which can rupture cells.

The above-described device and method of the invention provides means for producing injury to single, selected microvessels in the depth of the cortex using ultrashort laser-induced photodisruption. This model produces three types of vascular damage: thrombosis, breach of the blood-brain barrier, and hemorrhage. Thrombosis of single vessels may be a good model of local blockages of the microvasculature that lead to small infarcts in the brain. Previous models of lacunes and microinfarcts involved the systemic injection of small clotting agents such as microspheres or other emboli. The locations of the occlusions are random and unpredictable, and infarcts must be located post-mortem by the tedious inspection of the entire brain after histological sectioning. Using the inventive method and model, single microvessel occlusions can be placed in a predictable manner in the cortex, allowing the subsequent cellular and physiological events to be systematically studied. Further, the inventive method permits real-time monitoring of physiological parameters amenable to fluorescence microscopy (e.g. blood flow, intracellular $Ca^{2+}$ concentration, Reduced Nicotinamide Adenine Dinucleotide/Nicotinamide Adenine Dinucleotide (NADH/$NAD^+$) ratio, or the transmembrane voltage.). Similarly, vessel ruptures can be investigated in controlled experiments. Microvessels can be ruptured throughout the cortex to model the nature of hemorrhages that are detected in human brains by MRI. A third modality of vascular injury produced by the inventive device and method is the transient disruption of the blood-brain barrier leaving an intact vessel. The present invention can be used to study the effects of leaking blood plasma and its constituents into the neuronal parenchyma with and without ischemia.

By coupling real-time TPLSM with ultrashort laser photodisruption, the occlusions and hemorrhages in vessels can be monitored as they are formed. In addition, RBC velocities in the intact vessels surrounding an occluded microvessel can be measured.

The device and method of the present invention provide novel means for observing in real time and furthering the understanding of mechanisms and treatment of stroke and vascular dementia in the brain, and of vascular disease in other parts of the body, using animal models. The ability to induce and study vascular disorders in real time will provide means for evaluating treatments which can prevent, limit and/or reverse the damage caused by stroke and similar vascular insults in the brain and other organs within the body.

Other embodiments and modifications of the present invention will occur readily to those of ordinary skill in the art in view of these teachings. Therefore, this invention is to be limited only by the following claims which include all such other embodiments and modifications when viewed in conjunction with the above specification and accompanying drawings.

References (incorporated herein by reference)

1. N. Heye and J. Cervos-Navarro, "Microthromboemboli in acute infarcts: analysis of 40 autopsy cases," *Stroke* 27(3), 431-4. (1996).
2. G. J. del Zoppo and T. Mabuchi, "Cerebral microvessel responses to focal ischemia," *J Cereb Blood Flow Metab* 23(8), 879-94. (2003).
3. J. M. Wardlaw, P. A. Sandercock, et al., "Is breakdown of the blood-brain barrier responsible for lacunar stroke, leukoaraiosis, and dementia?," *Stroke* 34(3), 806-12. (2003).
4. G. J. del Zoppo, "Clinical trials in acute stroke: Why have they not been successful?," *Neurology* 51, S59-61. (1998).
5. P. Lipton, "Ischemic cell death in brain neurons," *Physiol Rev* 79(4), 1431-568. (1999).
6. D. E. McBean and P. A. Kelly, "Rodent models of global cerebral ischemia: a comparison of two-vessel occlusion and four-vessel occlusion," *Gen Pharmacol* 30(4), 431-4. (1998).
7. L. Wei, C. M. Rovainen, et al., "Ministrokes in rat barrel cortex," *Stroke* 26, 1459-1462. (1995).
8. L. Wei, J. P. Erinjeri, et al., "Collateral growth and angiogenesis around cortical stroke," *Stroke* 32(9), 2179-84. (2001).
9. A. Tamura, D. I. Graham, et al., "Focal cerebral ischaemia in the rat: 1. Description of technique and early neuropathological consequences following middle cerebral artery occlusion," *J Cereb Blood Flow Metab* 1(1), 53-60. (1981).
10. S. T. Chen, C. Y. Hsu, et al., "A model of focal ischemic stroke in the rat: reproducible extensive cortical infarction," *Stroke* 17(4), 738-43. (1986).
11. E. Busch, K. Kruger, et al., "Reperfusion after thrombolytic therapy of embolic stroke in the rat: Magnetic resonance and biochemical imaging," *Journal of Cerebral Blood Flow and Metabolism* 18(4), 407-418. (1998).
12. P. D. Lyden and B. Hedges, "Protective effect of synaptic inhibition during cerebral ischemia in rats and rabbits," *Stroke* 23, 1463-1469. (1992).
13. P. D. Lyden, J. A. Zivin, et al., "Quantitative effects of cerebral infarction on spatial learning in rats," *Experimental Neurology* 116(2), 122-132. (1992).
14. P. D. Lyden, L. M. Lonzo, et al., "Effect of ischemic cerebral volume changes on behavior," *Behavioral Brain Research* 87, 59-67. (1997).
15. M. Kudo, A. Aoyama, et al., "An animal model of cerebral infarction. Homologous blood clot emboli in rats," *Stroke* 13(4), 505-8. (1982).
16. K. Overgaard, "Thrombolytic therapy in experimental embolic stroke," *Cerebrovasc Brain Metab Rev* 6(3), 257-86. (1994).
17. K. Krueger and E. Busch, "Protocol of a thromboembolic stroke model in the rat: review of the experimental procedure and comparison of models," *Invest Radiol* 37(11), 600-8. (2002).
18. G. A. Rosenberg, S. Mun-Bryce, et al., "Collagenase-induced intracerebral hemorrhage in rats," *Stroke* 21(5), 801-7. (1990).
19. R. M. Dijkhuizen, M. Asahi, et al., "Rapid breakdown of microvascular barriers and subsequent hemorrhagic transformation after delayed recombinant tissue plasminogen activator treatment in a rat embolic stroke model," *Stroke* 33(8), 2100-4. (2002).
20. W. Deinsberger, J. Vogel, et al., "Experimental intracerebral hemorrhage: description of a double injection model in rats," *Neurol Res* 18(5), 475-7. (1996).
21. S. L. Hickenbottom, J. C. Grotta, et al., "Nuclear factor-kappaB and cell death after experimental intracerebral hemorrhage in rats," *Stroke* 30(11), 2472-7; discussion 2477-8. (1999).
22. J. P. Pooler and D. P. Valenzeno, "Dye-sensitized photodynamic inactivation of cells," *Med Phys* 8(5), 614-28. (1981).
23. K. S. Herrmann, "Platelet aggregation induced in the hamster cheek pouch by a photochemical process with excited fluorescein isothiocyanate-dextran," *Microvasc Res* 26(2), 238-49. (1983).
24. B. D. Watson, W. D. Dietrich, et al., "Induction of reproducible brain infarction by photochemically initiated thrombosis," *Annals of Neurology* 17, 497-504. (1985).
25. B. Krammer, "Vascular effects of photodynamic therapy," *Anticancer Res* 21(6B), 4271-7. (2001).
26. W. D. Dietrich, M. D. Ginsberg, et al., "Photochemically induced cortical infarction in the rat. 1. Time course of hemodynamic consequences," *J Cereb Blood Flow Metab* 6(2), 184-94. (1986).
27. W. D. Dietrich, M. D. Ginsberg, et al., "Photochemically induced cortical infarction in the rat. 2. Acute and subacute alterations in local glucose utilization," *J Cereb Blood Flow Metab* 6(2), 195-202. (1986).
28. C. B. Schaffer, F. F. Ebner, et al., "Two-photon fluorescence microscopy of collateral blood flow following photothrombotic stroke in rat neocortex", Optical Society of America, Tuscon, Ariz. (2003).
29. C. B. Schaffer, F. F. Ebner, et al., "Arteriole blood flow reverses direction at the first branch that lies downstream from a localized photothrombotic clot", Society of Neuroscience, New Orleans, La. (2003).
30. C. B. Schaffer, P. S. Tsai, et al., "All optical thrombotic stroke model for near-surface blood vessels in rat: Focal illumination of exogenous photosensitizers combined with real-time two-photon imaging", Commercial and Biomedical Applications of Ultrafast Lasers III, San Jose, SPIE-International Society of Optical Engineering (2003).
31. U. Dirnagl, B. Kaplan, et al., "Continuous measurement of cerebral cortical blood flow by laser-doppler flowmetry in a rat stroke model," *J Cereb Blood Flow Metab* 9, 589-596. (1989).
32. H. Nakase, T. Kakizaki, et al., "Use of local cerebral blood flow monitoring to predict brain damage after disturbance to the venous circulation: cortical vein occlusion model by photochemical dye," *Neurosurgery* 37(2), 280-5; discussion 285-6. (1995).
33. M. Hoehn-Berlage, D. G. Norris, et al., "Evolution of regional changes in apparent diffusion coefficient during focal ischemia of rat brain: the relationship of quantitative diffusion NMR imaging to reduction in cerebral blood flow and metabolic disturbances," *J Cereb Blood Flow Metab* 15(66), 1002-1011. (1995).
34. G. Marchal, A. R. Young, et al., "Early postischemic hyperperfusion: pathophysiologic insights from positron emission tomography," *J Cereb Blood Flow Metab* 19(5), 467-82. (1999).
35. M. Ishikawa, E. Sekizuka, et al., "Platelet adhesion and arteriolar dilation in the photothrombosis: observation with the rat closed cranial and spinal windows," *J Neurol Sci* 194(1), 59-69. (2002).
36. J. Seylaz, R. Charbonne, et al., "Dynamic in vivo measurement of erythrocyte velocity and flow in capillaries and of microvessel diameter in the rat brain by confocal laser microscopy," *J Cereb Blood Flow Metab* 19(8), 863-70. (1999).
37. E. Pinard, Nallet, et al., "Penumbral microcirculatory changes associated with peri-infarct depolarizations in the rat," *Stroke* 33, 606-612. (2002).
38. L. Wei, K. Craven, et al., "Local cerebral blood flow during the first hour following acute ligation of multiple arterioles in rat whisker barrel cortex," *Neurobiol Dis* 5(3), 142-50. (1998).
39. W. Denk, J. H. Strickler, et al., "Two-photon laser scanning fluorescence microscopy.," *Science* 248, 73-76. (1990).
40. W. Denk, "Two-photon scanning photochemical microscopy: Mapping ligand-gated ion channel distributions," *Proceedings of the National Academy of Sciences USA* 91, 6629-6633. (1994).
41. D. Kleinfeld, P. P. Mitra, et al., "Fluctuations and stimulus-induced changes in blood flow observed in individual capillaries in layers 2 through 4 of rat neocortex," *Proceedings of the National Academy of Sciences USA* 95, 15741-15746. (1998).
42. D. Kleinfeld and W. Denk (2000). Two-photon imaging of neocortical microcirculation. *Imaging Neurons: A Laboratory Manual*. R. Yuste, F. Lanni and A. Konnerth. Cold Spring Harbor, Cold Spring Harbor Laboratory Press: 23.1-23.15.
43. N. Suhm, M. H. Gotz, et al., "Ablation of neural tissue by short-pulsed lasers—A technical report," *Acta Neurochirurgica* 138, 346-349. (1996).
44. F. H. Loesel, J. P. Fischer, et al., "Non-thermal ablation of neural tissue with femtosecond laser pulses," *Applied Physics B* 66, 121-128. (1998).
45. P. S. Tsai, B. Friedman, et al., "All-optical histology using ultrashort laser pulses," *Neuron* 39, 27-41. (2003).
46. S. Backus, R. Bartels, et al., "High-efficiency, single-stage 7-kHz high-average-power ultrafast laser system," *Optics Letters* 26, 465-467. (2001).
47. K. Svoboda, W. Denk, et al. "In vivo dendritic calcium dynamics in neocortical pyramidal neurons." *Nature* 385: 161-165. (1997).
48. J. G. Fujimoto, "Optical coherence tomography for ultrahigh resolution in vivo imaging", *Nature Biotechnology*, 21:11 pp. 1361-1367 (2003).

What is claimed is:

1. A method of producing spatially localized injury to vasculature in a live animal, the method comprising:
   targeting vasculature in three dimensions for photodisruption; and
   focusing ultrashort laser pulses on the targeted vasculature to produce localized photodisruption.

2. The method of claim 1, further comprising observing physiological parameters in the animal.

3. The method of claim 1, wherein the step of targeting comprises using a microscope objective.

4. The method of claim 3, wherein the microscope objective has a numerical aperture within a range of 0.1 to 1.3.

5. The method of claim 3, wherein the microscope objective is a component of a two-photon laser scanning microscope.

6. The method of claim 5, further comprising observing the target vasculature using the microscope simultaneously with the photodisruption.

7. The method of claim 1, further comprising observing the target vasculature using optical coherence tomography simultaneously with the photodisruption.

8. The method of claim 1, wherein the step of targeting comprises using optical coherence tomography.

9. The method of claim 1, wherein the laser pulses have an energy adapted to drive a nonlinear interaction within the target vasculature.

10. The method of claim 1, wherein the laser pulses have pulsewidths in a range from 10 femtoseconds to 100 picoseconds.

11. The method of claim 1, further comprising preparing the animal to provide optical access to the vasculature via a transparent window formed in the animal.

12. The method of claim 11, wherein the window is adapted to provide access for insertion of electrical probes.

13. The method of claim 1, further comprising injecting the animal with a substance for labeling the blood stream.

14. The method of claim 13, wherein the substance is a water-soluble fluorescent tracer or fluorescently-labeled erythrocytes.

15. The method of claim 1, further comprising measuring blood flow in the targeted vasculature.

16. The method of claim 1, wherein the localized injury comprises vascular damage of a type selected from among thrombosis, hemorrhage and breach of the blood-brain barrier.

17. A method for in vivo modeling of vascular disorder, comprising:
   preparing an animal for optical access to vasculature; and
   targeting vasculature in three dimensions for photodisruption; and focusing ultrashort laser pulses on the target vasculature to produce localized photodisruption, wherein the laser pulses have an energy adapted to drive a nonlinear interaction within the target vasculature.

18. The method of claim 17, wherein the step of targeting comprises using a microscope objective.

19. The method of claim 18, wherein the microscope objective has a numerical aperture within a range of 0.1 to 1.3.

20. The method of claim 18, wherein the microscope objective is a component of a two-photon laser scanning microscope.

21. The method of claim 20, further comprising observing the target vasculature using the microscope simultaneously with the photodisruption.

22. The method of claim 17, further comprising observing the target vasculature using optical coherence tomography simultaneously with the photodisruption.

23. The method of claim 17, wherein the step of targeting comprises using optical coherence tomography.

24. The method of claim 17, further comprising observing physiological parameters within the animal using one or a combination of two-photon laser scanning microscopy, magnetic resonance imaging, functional magnetic resonance imaging, multi-spectral intrinsic imaging, positron emission tomography, time resolved light scattering, Doppler flowmetry, and optical coherence tomography.

25. The method of claim 17, further comprising observing physiological parameters within the animal using post-mortem histology.

26. The method of claim 17, wherein the laser pulses have pulsewidths in a range from 10 femtoseconds to 100 picoseconds.

27. The method of claim 17, wherein preparing the animal comprises forming a window for optical access to the target vasculature.

28. The method of claim 17, wherein preparing the animal comprises injecting the animal with a substance for labeling the blood stream.

29. The method of claim 28, wherein the substance is a water-soluble fluorescent tracer or fluorescently-labeled erythrocytes.

30. The method of claim 17, further comprising measuring blood flow in the targeted vasculature.

31. The method of claim 17, wherein the localized photodisruption comprises vascular damage of a type selected from among thrombosis, hemorrhage, and breach of the blood-brain barrier.

32. A method for observing vascular disease or injury in real time, comprising:
 preparing an animal for optical access to vasculature; and
 targeting vasculature in three dimensions for photodisruption;
 focusing ultrashort laser pulses on the target vasculature to produce localized photodisruption, wherein the laser pulses have an energy adapted to drive a nonlinear interaction within the target vasculature; and observing physiological parameters of the animal before, during and after photodisruption.

33. The method of claim 32, wherein the step of targeting comprises using a microscope objective.

34. The method of claim 33, wherein the microscope objective has a numerical aperture within a range of 0.1 to 1.3.

35. The method of claim 33, wherein the microscope objective is a component of a two-photon laser scanning microscope.

36. The method of claim 35, further comprising observing the target vasculature using the microscope.

37. The method of claim 33, further comprising observing the target vasculature using optical coherence tomography.

38. The method of either claim 36 or claim 37, wherein the step of observing is performed simultaneously with photodisruption.

39. The method of claim 33, wherein the step of targeting comprises using optical coherence tomography.

40. The method of claim 33, wherein observing comprises using one or a combination of two-photon laser scanning microscopy, magnetic resonance imaging, functional magnetic resonance imaging, multi-spectral intrinsic imaging, positron emission tomography, time resolved light scattering, Doppler flowmetry, and optical coherence tomography.

41. The method of claim 33, wherein observing after photodisruption comprises using post-mortem histology.

42. The method of claim 33, wherein the laser pulses have pulsewidths in a range from 10 femtoseconds to 100 picoseconds.

43. The method of claim 33, wherein preparing the animal comprises injecting the animal with a substance for labeling the blood stream.

44. The method of claim 43, wherein the substance is a water-soluble fluorescent tracer or fluorescently-labeled erythrocytes.

45. The method of claim 33, further comprising measuring blood flow in the targeted vasculature.

46. The method of claim 33, wherein the localized photodisruption comprises vascular damage of a type selected from among thrombosis, hemorrhage, and breach of the blood-brain barrier.

\* \* \* \* \*